United States Patent
Heeg et al.

(12)

(10) Patent No.: US 6,391,345 B1
(45) Date of Patent: May 21, 2002

(54) CRANBERRY SEED OIL, CRANBERRY SEED FLOUR AND A METHOD FOR MAKING

(76) Inventors: Tim Heeg, 1819 W. Old Shakopee Rd., #320, Bloomington, MN (US) 55431; Bernard G. Lager, II, 6506 Crest Ridge Ct., Wisconsin Rapids, WI (US) 54494

( * ) Notice: Subject to any disclaimer, the term of this patent is extended or adjusted under 35 U.S.C. 154(b) by 63 days.

(21) Appl. No.: 09/597,593

(22) Filed: Jun. 16, 2000

Related U.S. Application Data

(60) Provisional application No. 60/203,775, filed on May 12, 2000.

(51) Int. Cl.[7] ................................................ A61K 35/78
(52) U.S. Cl. ........................................ 424/732; 426/629

(58) Field of Search ................................. 424/732, 615, 424/629

(56) References Cited

PUBLICATIONS

Maneatis, J.G., "Low–Jitter Process–Independent DLL and PLL Based on Self–Biased Techniques", *IEEE Journal of Solid–State Circuits,* 31 (11), pp. 1723–1732, (Nov. 1996).

*Primary Examiner*—Jean C. Witz
(74) *Attorney, Agent, or Firm*—Schwegman, Lundberg, Woessner & Kluth, P.A.

(57) ABSTRACT

The present invention includes a cranberry seed oil, a cranberry flour and a method for making cranberry seed oil and flour. The cranberry seed oil comprises beta sitosterol and phosphatidylcholine.

4 Claims, 1 Drawing Sheet

CRANBERRY SEED OIL, CRANBERRY SEED FLOUR AND A METHOD FOR MAKING

This application claims the benefit of application Ser. No. 60/203,775, filed May 12, 2000.

BACKGROUND OF THE INVENTION

The present invention relates to cranberry seed oil, cranberry seed flour and to a method for making cranberry seed oil and cranberry seed flour and products comprising cranberry seed oil and cranberry seed flour.

American cranberries, *Vaccinium macrocarpon*, are native plants of open, acid peat bogs in North America. Cranberry plants are evergreen perennial vines that produce runners and upright branches with terminal flower buds.

Cranberries have historically been harvested and either ingested as whole berries, such as in cranberry sauce, or have been processed for their juice. Pulp remaining after cranberry juice extraction processing has historically been regarded as an undesirable waste product with little or no utility.

In the United States, cranberries are grown and are harvested in the Northeast, Northwest and Great Lakes regions. Cranberries ripen and are harvested in Autumn, which has made cranberries a holiday food. Cranberries have not changed significantly in appearance and nutritional value over time. Cranberries have typically been stored by freezing or drying the whole berries.

Cranberries have become a popular food only in recent years because cranberries have a very bitter taste. Historically, processors have not dealt well with the taste. Cranberries are known to contain quininic acid. It is the quininic acid that imparts to cranberries, the bitter taste. Cranberry juice has become more palatable because it is blended with other sugar-containing aqueous liquids.

Apart from an undesirable taste, quininic acid is believed to have nutraceutical properties. When ingested, quininic acid is converted to hippuric acid. Hippuric acid is believed to remove toxins from the bladder, kidneys, prostate and testicles.

SUMMARY OF THE INVENTION

In one product aspect, the present invention comprises a cranberry seed oil, the cranberry seed oil comprising oleic acid, linoleic acid, stearic acid, and alpha linolenic acid. In another product aspect, the present invention comprises products comprising the cranberry seed oil. The products comprise foods including foods for non-human animals, cosmetics, skin care products, sun screen, colorant agents, soap, hair care products, nutraceuticals such as antioxidants, and pharmaceuticals.

In its method aspect, the present invention comprises a method for making the cranberry seed oil. The method comprises cold pressing the oil from the seeds of cranberries.

In another method aspect, the present invention comprises a method for reducing waste products from cranberry juice processing. The method comprises providing cranberry pulp from a cranberry juice extraction process and extracting cranberry seed oil from the cranberry pulp. The seeds in the pulp are squeezed in a cold press at temperatures not exceeding about 100 degrees F. To obtain cranberry seed oil and cranberry seed flour, the solid residue product resulting from cranberry seed oil extraction is recovered from the cold press process and is dried.

In another method embodiment, the present invention comprises methods for making products comprising cranberry seed oil. The methods comprise blending the cranberry seed oil with other oils and non-oils materials such as soy, blueberry, pumpkin, aloe, sunflower, safflower, rose, saw palmetto, St John's wort, evening primrose, corn, and flax.

In another product aspect, the present invention comprises a cranberry flour. The cranberry flour comprises protein in a concentration of about 25 to 30 percent by weight, and total insoluble fiber of about 43 to 50% by weight. The cranberry flour has a potassium concentration of about 550 to 600 mg/100 g of flour and a calcium concentration of about 146.1 mg/100 g of flour.

Another embodiment of the present invention comprises a method for treating burns. The method comprises providing a blend of cranberry oil and saw palmetto. The blend is applied to an area of burned skin.

One other product of the present invention comprises mixture of cranberry oil and cranberry flour.

DETAILED DESCRIPTION

Figure 1:
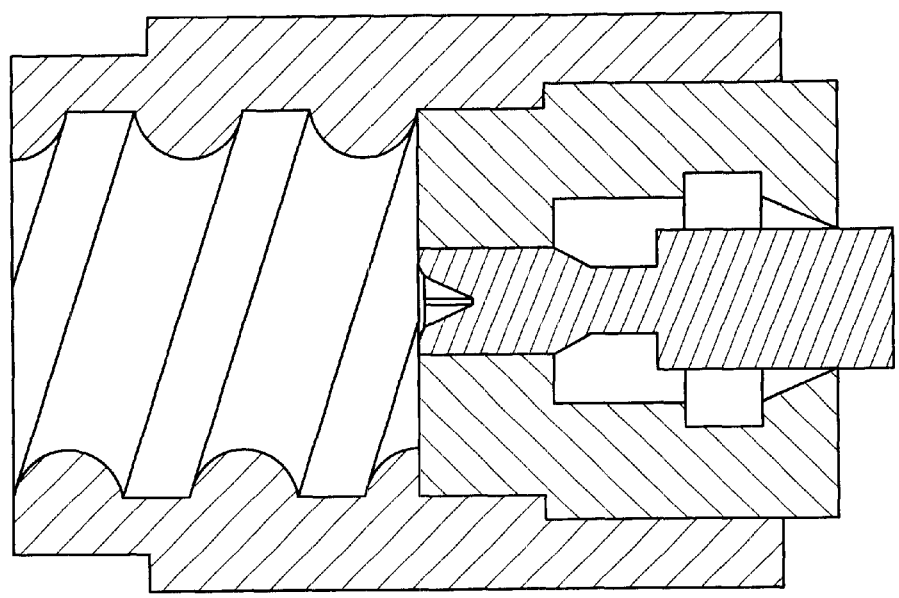
FIG. 1 is a cross sectional view of one embodiment of an expeller device used to extract oil from cranberry seeds.

In one product aspect, the present invention comprises an oil extracted from seeds of cranberries in a cold press extraction process. The oil has a substantially clear appearance with a pale yellow color. The cranberry oil comprises, in one embodiment, the following materials:

| Chemical in Cranberry Seed Oil Fatty Acid Comp. | % by Weight |
| --- | --- |
| 16:0 palmitic | 5.0 to 6.0 |
| 18:0 stearic | 1.0 to 2.0 |
| 18:1 oleic | 20 to 25 |
| 18:2 linoleic | 35 to 40 |
| 18:3 linolenic (alpha) | 30 to 35 |
| 20:0 arachidic | 0.13 |
| 20:1 gadoleic | 0.20 |
| 20:5 (n-3) | 0.32 |
| 22:2 | 1.1 |
| Myristic | 0.01 |
| Pentadecanoic | 0.02 |
| Palmitoleic (trans) | 0.13 |
| Palmitoleic (cis) | 0.08 |
| 10-heptadecanoic | 0.03 |
| Gamma linolenic | 0.1 to 0.2 |
| Nonadecanoic | 0.1 to 0.2 |
| 11-transeicosenic | 0.22 |
| 11, 14 eicosandienoic | 0.1 |
| 11, 14, 17 eicosatrienoic | 0.01 |
| Eicosapentaenoic | 0.01 |
| Behenic | 0.03 |
| Erucic | 0.02 |
| Docosapentaenoic | 0.01 |
| Tricosanoic | 0.01 |
| Lignoceric | 0.02 |
| Nervonic | 0.02 |
| Free fatty acid peroxide value (meg/kg) | 12.0 |
| Free fatty acids | 0.55 |
| Pytosterols determined by GC/MS | |
| Campesterol/brassicasterol (mg/kg) | 66 |
| Stigmasterol (mg/kg) | 68 |
| Beta-sitosterol (mg/kg) | 1319 |

-continued

| Chemical in Cranberry Seed Oil Fatty Acid Comp. | % by Weight |
| --- | --- |
| Phospholipid determined by HPLC | |
| Phosphatidylinositiol (mg/kg) | 9.9 |
| Phosphatidylcholine (mg/kg) | 202.0 |
| Vitamin E Determined by HPLC | |
| Alpha-tocopherol (mg/kg) | 341 |
| Gamma-tocopherol (mg/kg) | 110 |
| Iodine value | 150.1 |
| Saturated fat/serving | 6.86 |
| Monosaturated fat/serving | 23.51 |
| Trans fatty acids | 0.13 |

As can be seen, the cranberry seed oil is a rich source of fatty acids having use in food, cosmetic, fragrance, soap and skin and hair care formulations. Stigmasterol is an anti-stiffiess factor. Beta-sitosterol has use as an antihyperlipo-proteinemic agent. One or more of the campesterol, stigmasterol and beta-sitosterol have been found in seeds such as soy and wheat. It is believed that cranberry seed oil has inflammatory activity and may be useful in the treatment of gingivitis, rash, eczema, and other skin lesions. It is also believed that cranberry seed oil has use as a sun screen, in toothpaste, cremes for prevention of skin irritations, bath oil, antiperspirants, shampoos, and lipsticks. Cranberry oil has a high peroxide value which makes it suitable for soap production.

It has been observed that cranberry oil has absorbance in the UV-B range. It is this range that causes the greatest cellular damage. The cranberry oil can shield against UV-A induced damage by scattering light as well as by light spectrum absorption. The cranberry oil has, then activity as a broad spectrum UV protectant. The cranberry oil may be used alone or in combination with other conventional sunscreens.

These results indicate that the cranberry oil has use as a pharmaceutical or a source of materials having use as pharmaceuticals. The cranberry oil additionally has use in pharmaceutical preparations as a carrier or as an adjuvant of other type of dispersing agent. It is believed, for instance, that the cranberry oil has use in treating burns or sores or other lesions.

When used as a skin care product, such as a sunscreen or treatment for lesions, the cranberry oil may be blended with other ingredients. These other ingredients include emulsifiers. The emulsifiers may be used to make an oil-in-water emulsion or a water-in-oil emulsion. Emulsifiers may be anionic, cationic or non-ionic and either in a liquid or a solid phase at room temperature. Suitable emulsifiers include sorbitan esters; polyglyceryl-3-distearate; carbomer; ceteareth-15; cetyl alcohol; cetyl phosphate; dimethicone copolyol phosphate; glycerol isostearate; hydrogenated lecithin; laureth-12; PEG-20 distearate; PEG-8 oleate; PEG-40 sorbitan diisostearate; polyglyceryl-10 distearate; polysorbate 20; polysorbate 80; PPG-7 lauryl ether; sodium laureth sulfate; sorbitan sesquioleate; and acrylates/C(10–30) alkyl acrylate cross polymer.

Emollients may also be added to the skin care product. Emollients are oleaginous or oily substances which help smooth and soften the skin. Emollients include mineral oil, lanolin oil, coconut oil, cocoa butter, olive oil, almond oil, macadamia nut oil, aloe extracts such as aloe vera lipoquinone, synthetic jojoba oil, natural sonora jojoba oils, safflower oil, corn oil, liquid lanolin, cottonseed oil and peanut oil.

The skin care products may also include a humectant. Humectants promote retention of water due to hygroscopic properties. Humectants include glycerin, polymeric glycols, mannitol and sorbitol. Skin care products may additionally include a dry-feel modifier such as starch, talc, or kaolin. Sunscreen products typically include a waterproofing agent. The waterproofing agent is capable of maintaining sunscreen effectiveness on skin following exposure to circulating water for at least about 80 minutes. Skin care products may also include antimicrobial preservatives, antioxidants, chelating agents, fragrances and insect repelling agents.

The phosphatidylinositiol and phosphatidylcholine and tocopherols have use as nutraceuticals. The phosphatidylcholine, also known as lecithin, is found in human beings in the nervous system and the brain. Lecithin also has use as an edible and digestible surfactant. It is usable in manufacturing foods such as margarine and chocolate. Lecithin is a natural antioxidant that can increase oil stability and shelf life. Lecithin also has use in pharmaceuticals, cosmetics, skin care, and in treating leather and textiles.

Cranberry oil has a very high concentration of gamma tocopherol. This level is much higher than is found in oils such as safflower and grape, which are 11 and 33, respectively. The gamma tocopherol has the most antioxidant capacity of all of the tocopherols and contributes to the stability of highly unsaturated oils in the cranberry oil. It is believed that the presence of the high gamma tocopherol concentration makes cranberry oil an excellent additive to animal food-both human and non-human. The gamma tocopherol may be as important as alpha tocopherol in preventing degenerative diseases.

Cranberry oil has a high linolenic acid content. Linolenic acid has been implicated as a food additive and nutraceutical in preventing coronary heart disease and cancer. Cranberry oil also has a high polyunsaturated: saturated ratio in a neutral lipid fraction, of 10:1. This ratio is regarded as having value in reducing serum cholesterol, atherosclerosis and in preventing heart disease.

Cranberry oil has a yellow color which indicates a presence of carotenoids. The carotenoids are usable as colorant substitutes for materials such as carotenes, annotos, and apocarotenals used in the nutraceutical and oil industries.

The cranberry oil is also believed to have use in hair care products, imparting a luster and body to hair. The cranberry oil also has use in essences and flavonoids. The cranberry oil is usable as a stand-alone product. The cranberry is also usable when used in combination with oils such as strawberry oil, raspberry oil, hazelnut oil, blueberry oil and other oil combinations.

In one embodiment, the cranberry oil is blended with saw palmetto and is used as a treatment for burns and lesions when applied topically. It is believed that the combination oils may have synergistic properties due to an interaction of complementary ingredients.

The cranberry oil is extracted from cranberry seeds, which are left over after raw cranberries are "juiced"; that is, cranberry oil is squeezed out of, or otherwise extracted from, the cranberry seeds. The cranberry seeds are separated by methods conventionally known.

The cranberry oil is extracted from cranberry seeds using a cold press process. In particular, in one embodiment, cranberry seeds, separated from pulp waste obtained from cranberry juicing processes are used as a substrate for pressing in the process of the present invention. Cranberry pulp suitable for use in the present invention includes waste pulp resulting from virtually any juice extraction process. The cranberry pulp waste includes cranberry seed and cranberry fiber not used to make juice.

In one embodiment, the cranberry seed is passed through a Komet screw oil expeller, Model DD 85, manufactured by IBG Monforts GmbH & Co. One embodiment of the expeller accompanies this application as FIG. 1. The expeller includes a barrel that houses a screw for pressing the cranberry seed. A die is positioned at the end of the barrel. It is between the screw and the die where the oil squeezing process occurs. The seed is fed to the screw through a hopper. As the seed is transported to the die, the seed is mixed and pressurized.

The cranberry oil of the present invention is extracted from cranberry seeds that comprise a portion of the cranberry pulp. The seed oil is extracted at an ambient temperature, such as a temperature of about 80 to 90 degrees Fahrenheit. The oil extraction temperature is less than 125 degrees Fahrenheit. The speed setting for the screw expeller is within a range of 1.0 to 6.0.

While a Komet expeller is described, it is understood that other cold press devices are suitable for use in the present invention. Other cold presses include those presses conventionally used for extraction of soy, sunflower, and corn oil. What is important in the process of the present invention is that the cold press temperature not exceed 125 degrees F.

While cold pressing is described, it is believed that other oil extraction processes are usable to extract oil of the present invention. These other oil processes include solvent-based extraction, centrifugal, high pressure, osmosis, preheating, and filtration fractionation. One benefit of using the cold pressing process is that the process product is not limited to a versatile oil.

Oil extracted from cranberry seeds has a long shelf life due to the high concentration of antioxidants in the oil. The oil may be stored in bulk tanks or in containers of 1 gallon or less. The oil may be encapsulated alone or may be tableted or encapsulated as an ingredient in another nutraceutical or pharmaceutical. As discussed, the oil may be blended with other ingredients to make a skin care product, food, nutraceutical or pharmaceutical.

In addition to cranberry oil, the expeller produces a cranberry meal or cranberry flour. This result is surprising in that a single process for cranberry waste products yields two products, flour and oil, that have many uses. For some embodiments, the cranberry flour is blended with a desired quantity of cranberry oil or strawberry oil or blueberry oil or other oil or combination of oils to make a product having desirable pharmaceutical or nutraceutical of food additive or cosmetic properties.

In one embodiment, the cranberry flour has a moisture of about 5.4% by weight. Other materials in the cranberry flour include the following:

| Component | % by Weight |
|---|---|
| Protein | 25.84 |
| Fat | 3.77 |
| Ash | 2.69 |
| Total fiber | 51.06 |
| Soluble fiber | 5.13 |
| Insoluble fiber | 45.93 |
| Bulk density | 74.4 gr/100 cc |
| Sodium | 13.49 mg/100 g |
| Potassium | 568.4 mg/100 g |
| Calcium | 146.1 mg/100 g |
| Iron | 3.41 mg/100 g |

As can be seen, the flour is an excellent source of dietary calcium, potassium and iron. The flour is also an excellent source of dietary insoluble fiber.

The flour may be packaged as a free-flowing material in bulk or may be encapsulated or tableted using conventional methods.

The extraction process produces flour and oil. For a combined weight of 100 lbs, the oil content may range from about 10 lbs to 50 lbs.

Although the present invention has been described in detail with particular reference to these embodiments, other embodiments can achieve the same results. Variations and modifications of the present invention will be obvious to those skilled in the art, and it is intended to cover in the appended claims all such modifications and equivalents. The entire disclosures of all references, applications, patents and publications cited above are hereby incorporated by reference.

What is claimed is:

1. A cranberry seed flour, comprising:

insoluble fiber in a concentration of about 40 to 50% by weight of the flour.

2. The cranberry flour of claim 1 and further comprising calcium in a concentration of about 140 to 160 mg/100 g of flour.

3. The cranberry flour of claim 1 and further comprising potassium in a concentration of about 550 to 600 mg/100 g of flour.

4. The cranberry flour of claim 1 wherein the bulk density of the flour is about 70 to 80 grams per 100 cubic centimeters.

* * * * *